United States Patent [19]
Diederich

[11] Patent Number: 5,620,479
[45] Date of Patent: Apr. 15, 1997

[54] METHOD AND APPARATUS FOR THERMAL THERAPY OF TUMORS

[75] Inventor: Chris J. Diederich, Novato, Calif.

[73] Assignee: The Regents of the University of California, Oakland, Calif.

[21] Appl. No.: 383,472

[22] Filed: Jan. 31, 1995

Related U.S. Application Data

[63] Continuation-in-part of Ser. No. 332,997, Nov. 1, 1994, which is a continuation-in-part of Ser. No. 291,336, Aug. 17, 1994, abandoned, which is a continuation-in-part of Ser. No. 83,967, Jun. 25, 1995, Pat. No. 5,391,197, which is a continuation-in-part of Ser. No. 976,232, Nov. 13, 1992, abandoned.

[51] Int. Cl.$^6$ .............................. A61F 7/00; A61B 17/20
[52] U.S. Cl. ........................ 607/97; 607/154; 607/105; 604/22; 604/28
[58] Field of Search ........................ 604/53, 113, 28; 607/101, 102, 97, 104, 105, 154, 156, 113, 116, 22

[56] References Cited

U.S. PATENT DOCUMENTS

| | | |
|---|---|---|
| 4,312,364 | 1/1982 | Convert et al. . |
| 4,462,408 | 7/1984 | Silverstein et al. . |
| 4,586,512 | 5/1986 | Do-huu et al. . |
| 4,671,293 | 6/1987 | Shaulov . |
| 4,800,899 | 1/1989 | Elliot . |
| 4,907,589 | 3/1990 | Cosman . |
| 4,961,435 | 10/1990 | Kitagawa et al. . |
| 5,002,058 | 3/1991 | Martinelli . |
| 5,070,879 | 12/1991 | Herres . |
| 5,167,231 | 12/1992 | Matsui . |
| 5,344,435 | 9/1994 | Turner et al. . |
| 5,351,691 | 10/1994 | Brommersma . |
| 5,391,197 | 2/1995 | Burnette et al. . |

FOREIGN PATENT DOCUMENTS

| | | |
|---|---|---|
| 3719705 | 12/1987 | Germany . |
| 1266548 | 10/1986 | U.S.S.R. . |
| 1528509 | 12/1989 | U.S.S.R. . |
| 1648504 | 5/1991 | U.S.S.R. . |
| WO02779 | 7/1985 | WIPO . |

OTHER PUBLICATIONS

Hynynen et al., Small Cylindrical Ultrasound Sources for Induction of Hyperthermia Via Body Cavities or Interstitial Implants, Int. J. Hyperthermia, 1993, vol. 9, No. 2, 263–274.

(List continued on next page.)

*Primary Examiner*—John D. Yasko
*Assistant Examiner*—Perry E. Van Over
*Attorney, Agent, or Firm*—John P. O'Banion

[57] ABSTRACT

An ultrasound applicator for thermal therapy, having a multi-element array of plastic or rubber coated piezoceramic tubular transducers, each with separate power control and supported by a coaxially disposed semi-flexible central tube, which can be placed directly within the tumor or target region, or within a body lumen such as a blood vessel or body cavity such as the urethra, or within a separate delivery catheter or system. Thermocouple sensors embedded in the coating over each transducer can be used for continuous monitoring of the tissue/applicator interface temperatures for feedback control of the power applied to each transducer. The transducers are resonant across the wall thickness and radiate energy in the radial direction. The applicator provides an air-cooling system which can control the temperature of the transducers and thereby improve heating characteristics. In the primary configuration, the central tube is a catheter which is compatible with remote afterloaders and standard brachytherapy technology, and facilitates the delivery of interstitial thermal therapy in conjunction with simultaneous brachytherapy or radiotherapy from within the applicator. For alternate forms of therapy or when the radiation source is not in the catheter, the central catheter can be used to circulate temperature regulated air or water to control the surface temperature of the applicator, or to infuse drugs. Further, the applicator can be placed within a thin-walled implant catheter and flushed with temperature controlled circulating coupling fluid to control the temperature of the catheter/tissue interface, or used in conjunction with other conventional delivery systems, instead of being used interstitially.

33 Claims, 7 Drawing Sheets

OTHER PUBLICATIONS

Hynynen, The Feasibility of Interstitial Ultrasound Hyperthermia, Am. Assoc. Phys. Med., Jul/Aug 1992.

Diederich et al., Ultrasound Technology for Interstitial Hyperthermia, Medical Radiology Interstitial and Intracavitary Thermoradiotherapy, Springer–Verlag 1993.

Diederich, C.J., A Design Study of Ultrasound Applicators For Interstitial Hyperthermia, NAH Annual Meeting 1993.

Diederich, C.J., A Theoretical–Study of Ultrasound Interstitial Hyperthermia, Medical Physics, vol. 19, No. 3, May/Jun. 1992.

Diederich, C.J., The Design of Ultrasound Applictors for Interstitial Hyperthermia, IEEE Ultrasonic Symposium, Nov. 1993.

METHOD AND APPARATUS FOR THERMAL THERAPY OF TUMORS

CROSS-REFERENCE TO RELATED APPLICATIONS

This application is a continuation-in part of application Ser. No. 08/332,997, filed on Nov. 1, 1994, which is a continuation-in-part of Ser. No. 08/291,336 filed on Aug. 17, 1994, which is a continuation-in-part of Ser. No. 08/083,967 filed on Jun. 25, 1995 now U.S. Pat. No. 5,391,197, which is a continuation-in-part of Ser. No. 07/976,232 filed on Nov. 13, 1992 now abandoned.

BACKGROUND OF THE INVENTION

1. Field of the Invention

This invention pertains generally to treatment of tumors and benign tissues using thermal therapy, and more particularly to a method and apparatus for applying interstitial hyperthermia, simultaneous thermoradiotherapy, simultaneous thermobrachytherapy, or thermal ablation for the treatment of cancer or benign diseases.

2. Description of the Background Art

Localized hyperthermia may be used as an adjuvant to radiation treatment and chemotherapy in the clinical management of cancer. Traditionally, heat and radiation have been applied sequentially (hyperthermia immediately pre/post radiotherapy), using special applicators to apply heat-inducing energy within a tumor, raising the temperature to approximately 42.5° to 45° C., and maintaining the temperature for approximately 30 to 60 minutes. Recent biological studies and clinical evidence, however, have indicated a significant enhancement of combined therapy if applied concurrently over a longer duration. This form of therapy would be most applicable to interstitial therapy where the catheters are implanted directly within the tissues to be treated, thereby localizing the heat and radiation within the target tissue and reducing normal tissue toxicity.

Interstitial heating remains a treatment of choice for many tumors, despite the invasive nature of the technique, since the heating and/or radiation sources are inserted directly into the tumor, thereby localizing heat within the target volume and sparing more of the surrounding normal tissue. These methods are most often used for treating bulky or unresectable deep-seated tumors surrounded by sensitive normal tissues (i.e. brain, neck), or for sites in the pelvis (i.e. prostate, cervix) which are difficult to localize by external methods. The implant catheters are inserted intraoperatively often using pre-planned trajectories that are determined primarily for the radiation dose patterns. The number and location of heat sources are dictated by the tumor geometry and the power deposition or heating capability of each source, and the remaining catheter tracks are generally used for thermometry measurements. Interstitial thermotherapy has traditionally been given "sequentially" to brachytherapy, with heating procedures performed immediately prior to insertion of the radioactive sources and after removal.

There are many interstitial heating technologies being used clinically or currently under development. Typically, interstitial techniques utilize the same catheters or needles for both heating and radiotherapy, but most of the technology is not amenable to concurrent insertion of radiation sources during thermal therapy. Conventional heating technologies employed for "sequential" interstitial thermal therapy include radiofrequency local current field (RF-LCF) electrodes, capacitively coupled RF electrodes, coaxial cable mounted microwave antennas, inductively heated ferromagnetic seeds, resistance wire, fiber-optic coupled lasers, and hot water tubes. Two techniques, however, have been adapted successfully for simultaneous therapy: (i) RF-LCF current heating, and (ii) use of conductive heating catheters.

RF-LCF heating devices use metal implant needles with electrical connections directly from the template, leaving the lumen available for simultaneous insertion of radiation sources, but require that a portion of the implant needles be designated for thermometry measurements. The RF-LCF approach has been shown to be efficacious in many clinical situations, but the heating dependence on needle alignment, appropriate needle pairing, and the inability to adjust the longitudinal heating pattern dictate that alternative techniques be investigated. In partial response to this need, it has been proposed to use alternating segmented RF electrodes (which are not compatible with insertion of radiation sources) with standard needles within the same implant array to improve longitudinal control.

Recent designs of open lumen conductive heating catheters, wherein transducers are placed within a brachytherapy implant catheter and surrounded by a coupling fluid, having multiple resistance-wire heating elements and built-in temperature sensing are being developed for concurrent therapy, but have not yet been implemented in the clinic. These conductive heating catheters have the potential for longitudinal control of heating but, since there is no power deposition in tissue, the use of these catheters is limited to clinical situations allowing for dense implant spacing (1 to 1.5 cm, large number of heat applicators) and lower per fusion targets. However, an attractive feature of this conductive technique is the possibility of parameter estimation in order to estimate minimum tumor temperatures for treatment control purposes.

Although efficacious in many clinical situations, none of the aforementioned methods and devices allow the power deposition to be easily varied along the length of the implant during the course of treatment to account for heterogeneities in tumor structure and dynamic changes in blood perfusion. Existing technologies require that the heating catheters be closely spaced, and are generally sensitive to the alignment and interaction of neighboring sources. This increases the number of catheters or needles which must be implanted for acceptable uniformity of heating, leaving few for temperature monitoring and control of the treatment. Further, the ability to improve control and penetration of the power deposition of interstitial applicators is a critical problem: in order to offer the best chances for a good clinical response, the whole tumor and tumor margins must be heated to therapeutic levels, with a steep transition to lower temperatures in the surrounding normal tissue. This criteria, combined with the often heterogeneous nature of the target tissue, dictate that control and penetration be improved. Recent efforts to improve control of the power deposition along the length include technology developments such as segmented RF electrodes and conductive sources. Special pre-wired implant templates and hardware/software configurations expedite treatment setup and allow for multiple needle activation schemes are offering improvement in control of the RF-LCF heating. In addition, the strategy of cooling the source surface to improve the radial heating distributions has been investigated for RF-LCF and microwave sources.

Accordingly, there is a need for a direct-coupled interstitial ultrasound applicator for the simultaneous delivery of hyperthermia and radiation therapy which provides for variable power deposition and accurate treatment control. The present invention, satisfies that need, as well as others, and overcomes the deficiencies in prior methods and devices.

SUMMARY OF THE INVENTION

The present invention pertains generally to an ultrasound applicator for thermal therapy of tumors and benign tissues using heat generated from acoustic energy, which includes a segmented array of individually controllable tubular ultrasound transducers through which an inner catheter extends. The applicator of the present invention can be used for (i) interstitial thermal therapy, (ii) interstitial thermal therapy in conjunction with simultaneous radiation therapy, or (iii) interstitial thermal therapy in conjunction with infusion of drugs, each of which can be effected by placing the applicator directly within the tumor or target region or within a body lumen such as a blood vessel or a body cavity such as the urethra. Alternatively, the applicator can be inserted into a fluid cooled brachytherapy catheter, or used in conjunction with other types of delivery systems, instead of being used interstitially.

By way of example, and not of limitation, an ultrasound applicator in accordance with the present invention comprises a multiple element array of piezoceramic or piezoelectric tubular transducers, each with separate power control, surrounded by thin layers of a biocompatible acoustic matching and electrically-insulating coating. A semi-flexible inner conduit comprising a catheter compatible with remote afterloaders and standard brachytherapy technology is coaxially disposed through each of the tubular transducers. Thermocouple temperature sensors are embedded in the coating over each transducer for continuous monitoring of the tissue/applicator interface temperatures and feedback control of the power applied to each transducer in the array. The transducers are resonant across the wall thickness and radiate energy in the radial direction. The power level to each transducer in the array is controlled separately and can be varied during treatment. In addition, if desired a temperature regulated gas can be circulated between the transducer and the inner catheter to control the applicator/tissue interface and improve heating distributions.

For interstitial thermal therapy, the applicator can be placed directly within the tumor or target region, with the plastic coated transducers forming the outer wall of the implant catheter. Therapy can be effected using low temperature heat (e.g., <45° C.), or high temperature (>45° C.) heat can be used for thermal ablation or inducing coagulation necrosis. If desired, performance of the applicator can be enhanced by circulating a coolant such as temperature regulated air (or other gas such as $CO_2$) or water through the inner catheter or between the inner catheter and transducers to control the surface temperature (e.g., cool) and extend the radial heating profile. Quite significantly, however, the applicator can be used for interstitial simultaneous thermoradiotherapy by inserting a radiation source into the inner catheter. This manner of use provides superior results for applications amenable to simultaneous interstitial heat with brachytherapy such as treatment of brain tumors or the like. Long term hyperthermia (e.g., 1 to 3 days) at temperatures above 41° C. given concurrently with radiation will dramatically improve tumor control. Another alternative interstitial approach would be to include apertures in the inner catheter and applicator body through which drugs can be infused into the tissue during heating.

Alternatively, the applicator can be inserted into a closed-end implant catheter or used in conjunction with other conventional delivery system instead of being directly inserted interstitially. For example, the applicator could be placed within a thin-walled implant catheter, Luer-locked into place, and flushed with temperature controlled circulating coupling fluid to control the temperature of the catheter/tissue interface. Since this approach is not amenable to simultaneous radiation therapy by means of the inner catheter, however, a coolant could be circulated through the inner catheter if desired, and returned within the implant catheter, flowing between the applicator and the plastic catheter wall. This approach increases the radial depth of therapeutic heating by forcing the maximum temperature away from the catheter surface, and allows the catheters to be spaced further apart thus requiring fewer needle insertions for a given implant volume.

A significant advantage of an applicator in accordance with the present invention, regardless of which of the foregoing treatment modes is employed, is that control of power to each individual transducer allows the tissue temperature to be controlled along the length of the applicator or catheter. This provides critical adjustability for accommodating irregular tumor geometry, heterogeneities of the tissue thermal properties, and dynamic changes in perfusion. In addition, the power deposition pattern is not dependent on the length of insertion or placement with regard to other catheters in the implant. Additionally, temperatures are measured at the tissue interface, providing important treatment information.

In response to the clinical needs previously identified, an object of the invention is to provide an ultrasound heating applicator having a linear array of small tubular ultrasound radiators, which is compatible with brachytherapy technology and which will be more effective for delivering concurrent interstitial thermoradiotherapy in high perfusion heterogeneous tissue volumes than existing technologies. A further object is to provide an applicator that can effectively localize a uniform heating pattern within an irregularly shaped, heterogeneous tumor volume while avoiding overheating the surrounding critical normal tissues. The advantages of implantable ultrasound applicators in accordance with the present invention further include: (1) the applicators may be spaced farther apart, requiring fewer needle insertions for a given implant volume, while providing improved homogeneity of the thermal dose distribution due to the penetration characteristics of ultrasound energy in soft tissues; (2) individual control of power for each tubular element will allow dynamic and spatial control of tissue temperature along the length of each applicator; (3) the heating pattern of each element is not dependent on depth of insertion in tissue nor on placement with regard to other heating catheters within the implant; (4) the length and number of transducer segments in each catheter can be selected to accommodate different size target volumes and the required resolution of power deposition control; (5) built-in temperature sensing can measure temperatures along the applicator/tissue interface; (6) this design will allow the simultaneous insertion of radiation sources without interruption of the heating. Furthermore, the thermal dose distributions attainable with these applicators can be enhanced by (i) treatment planning to optimize the stereotactic placement of the applicators based upon thermal and radiation dose prescriptions and (ii) automatic treatment control to optimally adjust the power to each transducer element. Implantable ultrasound applicators in accordance with the present invention have the potential to improve significantly the quality of treatment in terms of uniformity and increase in the minimum thermal dose delivered throughout the entire tumor volume. This should increase the number of patients that can be treated effectively with simultaneous interstitial thermoradiotherapy.

Another object of the invention is to apply controlled hyperthermia, thermoradiotherapy, or ablation in combination either external beam or separate interstitial source radiation.

Another object of the invention is to provide for increased penetration of heating energy to heat larger volumes per needle, requiring fewer needle insertions to apply therapy.

Another object of the invention is to provide an ultrasound heating applicator having an adjustable energy deposition pattern that can be dynamically modified.

Another object of the invention is to provide for controlled, uniform output from a plurality of transducer segments, allowing control of the heating distribution along the length of the applicator or combination of applicators.

Another object of the invention is to provide an ultrasound application having a linear array of tubular ultrasound transducer segments with separately controllable power levels.

Another object of the invention is to localize higher and more uniform thermal doses within a specified heterogeneous tumor volume.

Another object of the invention is to provide for simultaneous interstitial application of heat and radiation.

Another object of the invention is to provide an ultrasound applicator which is compatible with remote afterloaders.

Another object of the invention is to measure temperature at the tissue/applicator interface.

Another object of the invention is to provide for flexible mounting of tubular transducers on an inner catheter.

Another object of the invention is to provide an air space between the inner catheter and transducers.

Another object of the invention is to provide for gas or fluid cooling of the transducers and/or applicator wall to improve heating.

Another object of the invention is to provide the capability of varying drive frequency to vary penetration.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DESCRIPTION OF THE PREFERRED EMBODIMENTS

Referring more specifically to the drawings, for illustrative purposes the present invention is embodied in the apparatus generally shown in FIG. 1 through FIG. 5 and the corresponding method of use described herein. It will be appreciated that the apparatus may vary as to configuration and as to details of the parts and that the method may vary as to the steps and their sequence without departing from the basic concepts as disclosed herein.

Figure 1:
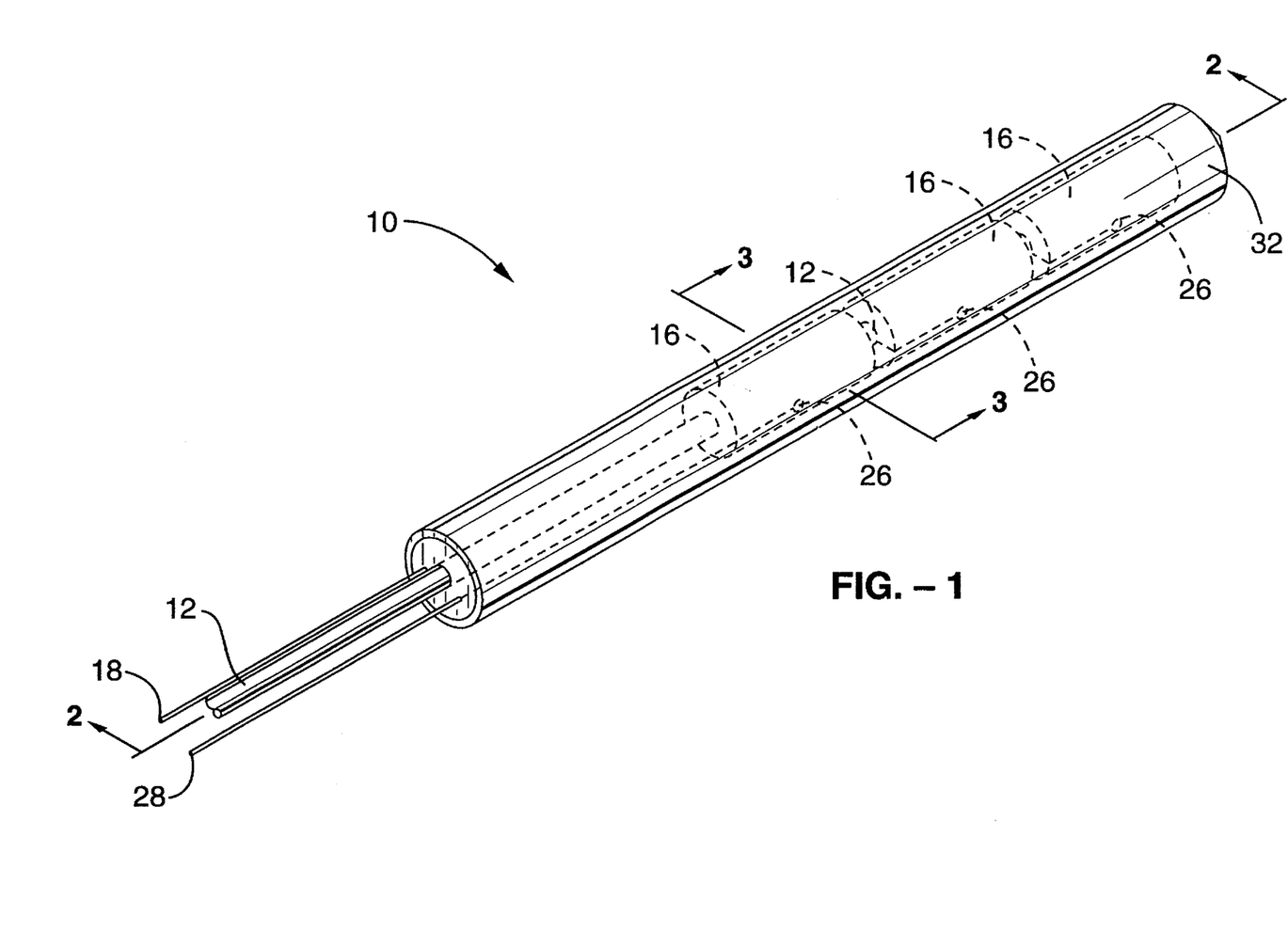
FIG. 1 is a perspective view of an ultrasound applicator in accordance with the present invention.
Figure 2:
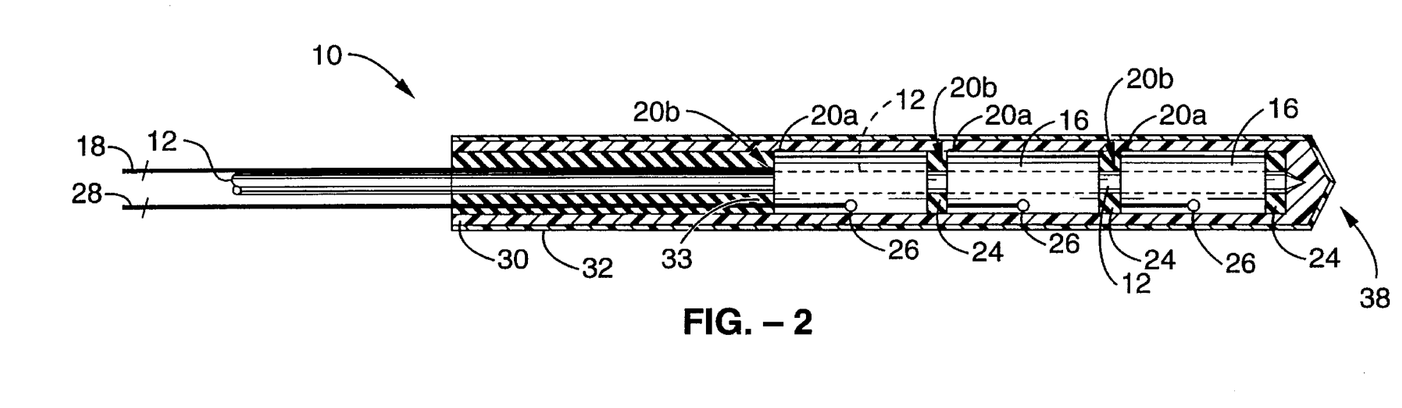
FIG. 2 is a longitudinal section view of an ultrasound applicator shown in FIG. 1 taken through line 2—2.
Figure 3:
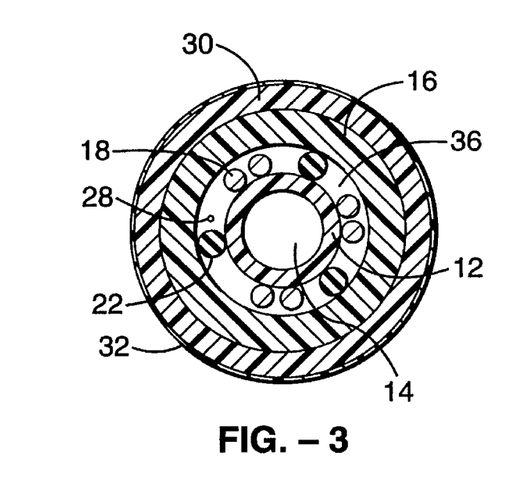
FIG. 3 is cross-sectional view of the ultrasound applicator shown in FIG. 1 taken through line 3—3.

Referring to FIG. 1 through FIG. 3, an ultrasound applicator 10 in accordance with the present invention preferably includes a cylindrical support member such as a tube, conduit or catheter 12 which is compatible with remote afterloaders and standard brachytherapy technology, such as a 16-g thin-walled polyurethane catheter or the like. Since catheter 12 includes a coaxial longitudinal inner lumen 14, a source of radiation, a drug or a coolant can be inserted therein. In the case of soft tumors such as found in the brain, catheter 12 is preferably a flexible polyurethane catheter as indicated above. For harder tumors which may require more rigidity, or for insertion of the applicator into an implant catheter or other delivery device where more rigidity is desired, thin-walled stainless steel hypodermic tubing or stiff conduits can be used instead.

Catheter 12 is coaxially disposed through a plurality of tubular piezoceramic transducers 16 which are spaced apart and electrically isolated as shown, thus forming a segmented array of tubular ultrasound transducers which radiate acoustical energy in the radial dimension. Transducers 16 are preferably made from type PZT-4, PZT-5A, PZT-7, PZT-8 or Lithium-Niobate type piezoceramic material to ensure high power output capabilities, and are available from Stavely Sensors, Inc. of East Hartford, CT or Valpey-Fischer Corp. of Hopkinton, Mass. The outer diameter is selected for the given clinical situation, and is typically in the range of approximately one to three millimeters. The length is also selected according to the clinical situation, and is typically approximately three to twenty millimeters.

Uniformity of transducer wall thickness is critical to the generation of uniform acoustic patterns. Further, the transducer material must be stable when exposed to the high activity $^{192}$Ir radiation sources (1 to 10 Ci) typical of pulsed LDR and HDR units.

The frequency range of the transducers will vary between approximately 5–12 MHz depending upon the specific clinical needs, such as tolerable outer diameter, depth of heating, and inner catheter outer diameter. Inter-transducer spacing is preferably approximately 0.5 mm. Those skilled in the art will appreciate that, while three transducers 16 are shown in FIG. 1 and FIG. 2, the number and length of transducers can be varied according to the overall desired heating length and spatial resolution of the applicator and depth of penetration desired. Note also that transducers 16 are preferably substantially cylindrical in shape to as to radiate a substantially symmetrical energy pattern, unless otherwise modified.

Each transducer 16 is electrically connected to a source of RF power through separate pairs of signal carrying wires 18, such as 4–8 mil silver wire or the like, soldered directly to the edges of the transducer surface to form connections 20a, 20b. One wire in the pair is connected to the edge of transducer 16 at its outer surface, while the other is connected to the edge of transducer 16 at its inner surface, although other connection points are also contemplated. Each wire 18 is routed through the center of the transducers between the outer wall of catheter 12 and the inner wall of the transducer as can be seen in FIG. 2, and from there to the connection point through the spaces between the individual transducer elements.

In order to ensure that each transducer 16 in the array is kept centered over catheter 12 while still maintaining flexibility and not impeding transducer vibration, a plurality of spacers 22 are disposed between the transducers and catheter 12. Preferably spacers 22 comprise thin rubber threads running longitudinally along catheter 12. However, where hypodermic tubing is used for catheter 12 as previously discussed, instead of using rubber as described above, transducers 16 could alternatively be mounted using a "spring-ground lead" comprising 3–4 mil stainless steel wire or the like wound to form a coaxial spring between the transducer and catheter 12 and soldered directly to the hypodermic tubing. The hypodermic tubing is then the common ground for all transducers, and the pressure contact of the spring to the transducer provides electrical contact, helps maintain alignment, and improves ultrasound field emission due to less clamping of the transducer and solder damage. This technique is particularly important for smaller diameter transducers (e.g., 1 to 2 mm OD), where soldering is difficult and often destroys activity in part of the transducer.

As indicated previously, transducers 16 are spaced off the tubular support member and, therefore, are "air backed" in the preferred embodiment. By air backing the transducers, the transducers produce more energy and have a more uniform energy distribution. In addition, it is preferred that the applicator be flexible so that it can bend. To ensure that the ends of each transducer is air backed and, accordingly, that each transducer is electrically and mechanically isolated, a conventional sealant 24 such as General Electric Silicon II gasket glue and sealant is injected around the exposed portions of catheter 12, wires 18, and spacers 22 between transducers 16. Sealant 24 acts as a glue and sealant, while at the same time, is sufficiently flexible to allow for the vibration of transducers 16 necessary for efficient radiation of ultrasonic energy. In addition, by placing the sealant only at the ends of the transducers, the redistribution of vibration from the ends of the transducers toward their centers (i.e., "clamping") is reduced.

As a means of monitoring the temperature of tissue surrounding the transducers, and to provide for temperature control and feedback, a plurality of small (e.g., 25.4 µm) thermocouple sensors 26, such as copper-constantan or constantan-maganin fine wire junctions, are placed along the outer surface of each transducer at points which are approximately one-half of the length of the transducer, and connected to individual temperature sensing wires 28 which run along one-half the length of the transducer and then through the space between catheter 12 and the transducers 16. A conventional acoustically compatible flexible epoxy 30 such as Epotek 310 available from Epoxy Technology is then spread over the transducers, thereby embedding the temperature sensors. The epoxy coated transducers are then sealed within an ultra thin walled (e.g., 0.5 to 3 mil) polyester heat shrink tubing 32 or the like, or inserted into a tight thin wall rubber or plastic tubing made from a material such as Teflon®, polyethylene, polyurethane, silastic, or the like. Preferably, after the heat shrink tubing is placed over the epoxy coated transducers, additional epoxy is injected into the heat shrink tubing. Then, when the tubing shrinks, the excess epoxy is forced out and a very thin layer of epoxy remains between the transducers and the heat shrink tubing. As can be further seen in FIG. 2, heat shrink tubing 32 extends beyond the area over transducers 16 and covers substantially the entire length of the applicator. To support heat shrink tubing 32 in the area beyond transducers 16, a filler 33 is placed around catheter 12 and between it and heat shrink tubing 32. Filler 33 can be epoxy such as epoxy 30, Teflon® tape, a support catheter, or other preferably flexible material.

Figure 4:
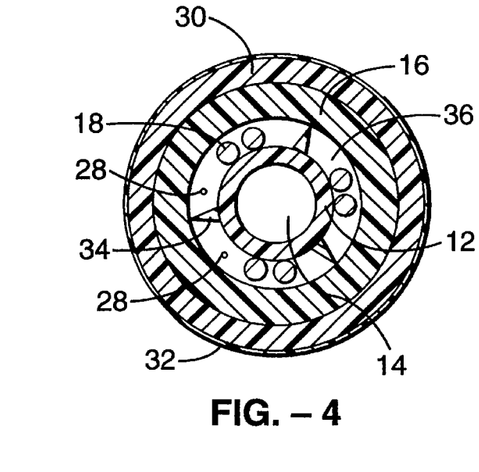
FIG. 4 is a cross-sectional view of an alternative embodiment of the ultrasound shown in FIG. 1, corresponding to the cross-section view of FIG. 3.

Referring also to FIG. 4, in order to improve the effective heating penetration of an applicator 10 in accordance with the present invention, a cooling scheme can be integrated within the transducer array to (i) remove transducer self-heating energy and (ii) potentially regulate the temperature of the tissue/applicator interface. Desirably, the radial heating profile can be extended by 20–30% when compared to ultrasound catheters without a cooling mechanism. However, due to size constraints, these devices are not amenable to the integration of a water cooling scheme along the outer transducer surface as in conventional applicators. For simultaneous therapy, catheter 12 must be compatible with remote afterloaders (e.g., 1.5 mm ID) and the outer applicator diameter must be acceptable to the surgeon (e.g., <2.6 mm OD). In addition, transducers 16 must remain air-backed to ensure high acoustic efficiency of the tubular radiators. By including spline segments or transducer standoffs 34 to permit temperature regulated air or gas to be circulated along the inner surface of the transducers 16 within the flow channels 36 between transducers 16 and catheter 12 defined by standoffs 34. These standoffs, which are preferably flexible and incorporated as an integral part of catheter 12, are also advantageous for ensuring air-backing, alignment of the transducers, and space for electrical wires. Catheter 12 can be custom extruded to include standoffs 34, as well as for minimum wall thickness and appropriate inner diameter for compatibility with conventional remote afterloading sources or other brachytherapy sources. After cooling the transducers 16, the air will flow into catheter 12 via multiple perforations (not shown) at the distal end 38, and exit the ultrasound applicator 10 through release ports (not shown). The flow channels 36 would be attached to a positive pressure gas cartridge (e.g., air or $CO_2$) with step down pressure regulators to very low pressures. Bottled gas is desirable since the water vapor is removed (desiccated), thereby avoiding condensation within the applicator due to gas expansion. Temperature regulation would be effected via thermoelectric heat-exchanger modules which are commercially available to control the temperature of circulating gas. In order to ensure clinical safety and air-tight integrity, this air-cooled embodiment of applicator 10 would preferably include a single body closed-end catheter as the biocompatible outer layer instead of shrink tubing 32, but would still be directly coupled to the tissue. Liquid cooling is also contemplated to be within the scope of the invention.

Figure 5:
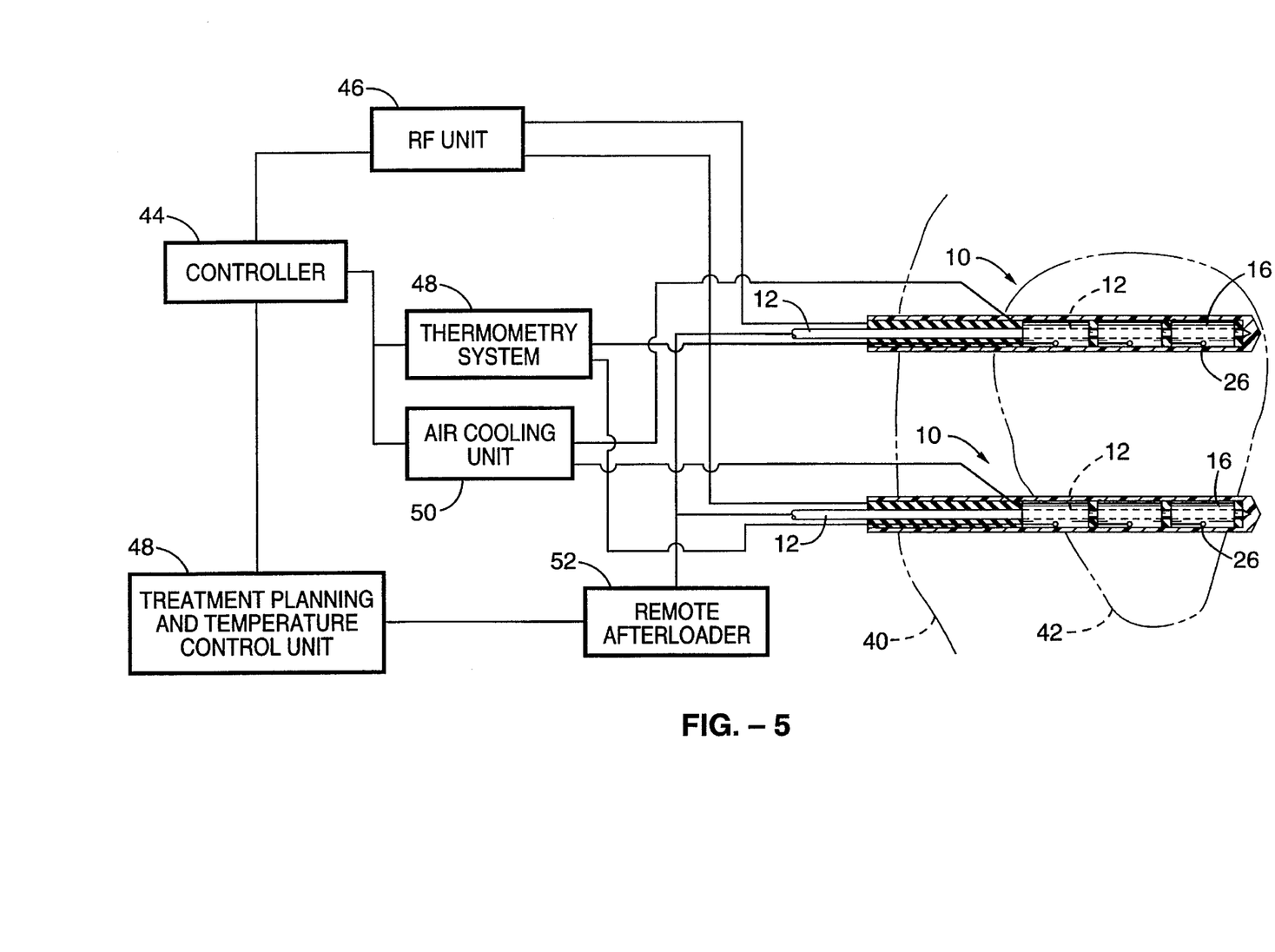
FIG. 5 diagrammatically shows a plurality of the applicators shown in FIG. 1 inserted into a tumor for treatment and coupled to a control and monitoring system.

Referring to FIG. 5, in the preferred method of treatment, one or more direct-coupled applicators 10 in accordance with the present invention are inserted through the body tissue of the patient 40 and into a tumor or target region 42 using a stylet (not shown) to stiffen the applicator during insertion. The RF power (frequency sweeped around the resonant frequency) level to each transducer 16 is controlled using the embedded thermocouple sensors 26 for temperature monitoring and feedback. Radiation sources or a remote afterloader is connected or placed within catheter 12 of the applicator to give the radiation dose directly to the tumor simultaneous with the heating. For applications not requiring radiation therapy, catheter 12 can support air/liquid cooling to control the applicator wall temperature as a means of increasing the radial depth of therapeutic heating from the individual transducers 16, or catheter 12 can include openings for infusion of drugs into the tissue. Additionally, in those applications where it may be desirable to control the temperature of the catheter/tissue interface, the applicator can be placed within a thin-walled plastic implant catheter, Luer-locked into place, and flushed with temperature controlled circulating coupling fluid to control the temperature of the catheter/tissue interface. The coolant would flow through the central lumen, out the tip, and return between the transducers and the implant catheter wall.

Also shown in FIG. 5 is a typical support system for the application and monitoring of hyperthermia treatments using ultrasound applicators in accordance with the present invention, which uses conventional and commonly available equipment. As can be seen, the system includes a controller 44, such as a personal computer, for data acquisition and display. RF unit 46, to which controller 44 is operatively connected, incudes a 32-channel RF amplifier, power monitoring module, and electrical impedance matching networks. The RF amplifier has the capability of variable center frequency, frequency modulation sweep rate, and power amplitude modulation for each channel, and is used to power the individual transducers. A thermometry system 48, which is also connected to controller 44, is connected to the temperature sensors 26 for monitoring the temperature of the applicator/tissue interface. An air cooling unit 52, for use in the manner previously described, can also be included and controlled by controller 44. Further, a remote afterloader 54 can be coupled to catheter 12 for radiation therapy. A treatment planning and temperature control unit 50, which is a DEC 3000/700 workstation or the like, is connected to controller 44 and afterloader 54 for overall system control, obtaining treatment planning information and exchanging temperature measurements for real-time updates of power levels and treatment. from the controller. A graphical interface would also be provided to display the tissue temperature rises, accumulated thermal dose, and relative applied power to each transducer. It will be noted, however, that the foregoing is by way of example only, and support system described above is neither critical nor forms a part of the claimed invention.

It will be appreciated that, where simultaneous application of radiation is not necessary or desirable, smaller applicators can be made either with smaller diameter catheters 12 or without inner lumen 14, in which a solid rod would be substituted for catheter 12. In this way, the applicator can be used for thermal therapy alone or to heat tissues during external beam therapy. Also, radiation sources could be modified to fit in smaller transducers. Further, the transducer wall can be scored (e.g., 30 to 90% cuts along the length) to reduce unwanted modes of vibration within the piezoceramic. In addition, the tubular transducers can be further segmented or sectored, and separate power control used to adjust power distribution in the angular expanse. Note also, that the scoring or removing sections of electrode transducer surfaces can be used to prevent energy from being radiated in those areas so as to protect sensitive tissues. Further, perforations or ports may be added to inject chemotherapeutic or other drugs which are activated either thermally (e.g., heat activated liposomes) or sonically.

The applicator of the present invention, when directly coupled in tissue, also lends itself to estimating/monitoring the local perfusion or thermal diffusivity of the tissue in regions immediately surrounding the applicator. The perfusion is a crucial parameter that is necessary to perform adequate treatment planning and control but is often unobtainable and varies during treatment. The procedure for estimating the thermal diffusivity or blood perfusion is as follows (i) immediately before, after or during a break in a therapeutic treatment the transducers are driven with RF power at a frequency substantially higher or lower than their resonant frequency so that all of the power is dissipated as resistive losses within the transducer material, no acoustic energy is emitted, and the temperature rises. In this fashion, the transducers are behaving as separately controllable conductive "hot" sources; (ii) the temperature of each transducer is monitored via the embedded thermocouple junctions; (iii) different power levels can be applied and the steady-state temperature rises recorded, with the slope of the rise being indicative of the thermal diffusion; (iv) the power level can be modulated to maintain a constant temperature rise, with the change in power required over time being indicative of the thermal diffusion; and (v) a pulse of known power can be applied and the thermal decay measured, since the rate of decay or thermal washout is a function of perfusion or thermal diffusion.

Additionally, the applicator of the present invention is well suited for thermal ablation an/or stereotactic thermal ablation. As an example of such an application, transrectal ultrasound imaging or other imaging methods would be used to determine the location of the target site (e.g., prostate, tumor) and the physician would stereotactically insert one or more applicators. Progress of the thermal ablation can be monitored using concurrent imaging of the tissue, and normal tissue compared with thermally coagulated tissue.

It is also be appreciated that, when used interstitially, the applicator of the present invention can be used to estimate tissue parameters by driving the transducers at a frequency where they do not resonate.

EXAMPLE 1

Applicator Fabrication

Prototype direct-coupled applicators were constructed using 2.5 mm diameter OD×0.33 mm wall thickness×10 mm long piezoceramic tubular transducers. Wire leads were soldered to each electrode surface. Two transducers were used for each applicator. The transducers were placed over a catheter which is compatible with remote afterloading sources. Single junction thermocouple sensors were placed over the center of each transducer, and then the applicator was coated with epoxy and plastic. The lead wires were connected to miniature coaxial cable at the proximal end of the applicator.

EXAMPLE 2

Acoustic and Thermal Models

The heating performance of these direct-coupled applicators was evaluated using computer simulation programs to calculate the acoustic fields and corresponding thermal distributions in tissue. The resulting power deposition $<q>$ (W m$^{-3}$) within the tissue or outer insulating layers produced by these cylindrical sources can be approximated by the following expression:

$$<q> = \frac{2\alpha f I_o r_o}{r} e^{-2\alpha f(r-r_o)}$$

where $I_o$ (W m$^{-2}$) is the acoustic intensity at the transducer surface, $r_o$ (m) is the radius of the transducer, $r$ (m) is the radial distance from the center of the transducer, $\alpha$ (Np m$^{-1}$ MHz$^{-1}$) is the amplitude attenuation coefficient of the tissue or outer coating, and f (MHz) is the frequency.

The self-heating of the transducer, attributed to inefficiency of power conversion, was also included in the model. This power deposition, as a function of applied electrical power or intensity at the applicator surface, is given as follows:

$$<q_t> = \frac{(1-\eta)P_L}{\pi(r_o^2 - r_i^2)} = \frac{(1-\eta)2\pi r_o I_o}{\eta\pi(r_o^2 - r_i^2)}$$

where $\eta$ is the efficiency of conversion from electrical input to acoustic output power, $P_L$ is applied electrical power per transducer length (W m−1), and $r_i$ is the inner radius of the transducer wall.

The temperature distributions resulting from the compiled power deposition patterns were calculated using the steady-state form of the bio-heat transfer equation (BHTE), a descriptive model which approximates tissue thermal characteristics. These simulations were configured to model the thermal properties of the multiple layers and the PZT transducer material.

EXAMPLE 3

Simulations

Figure 6:
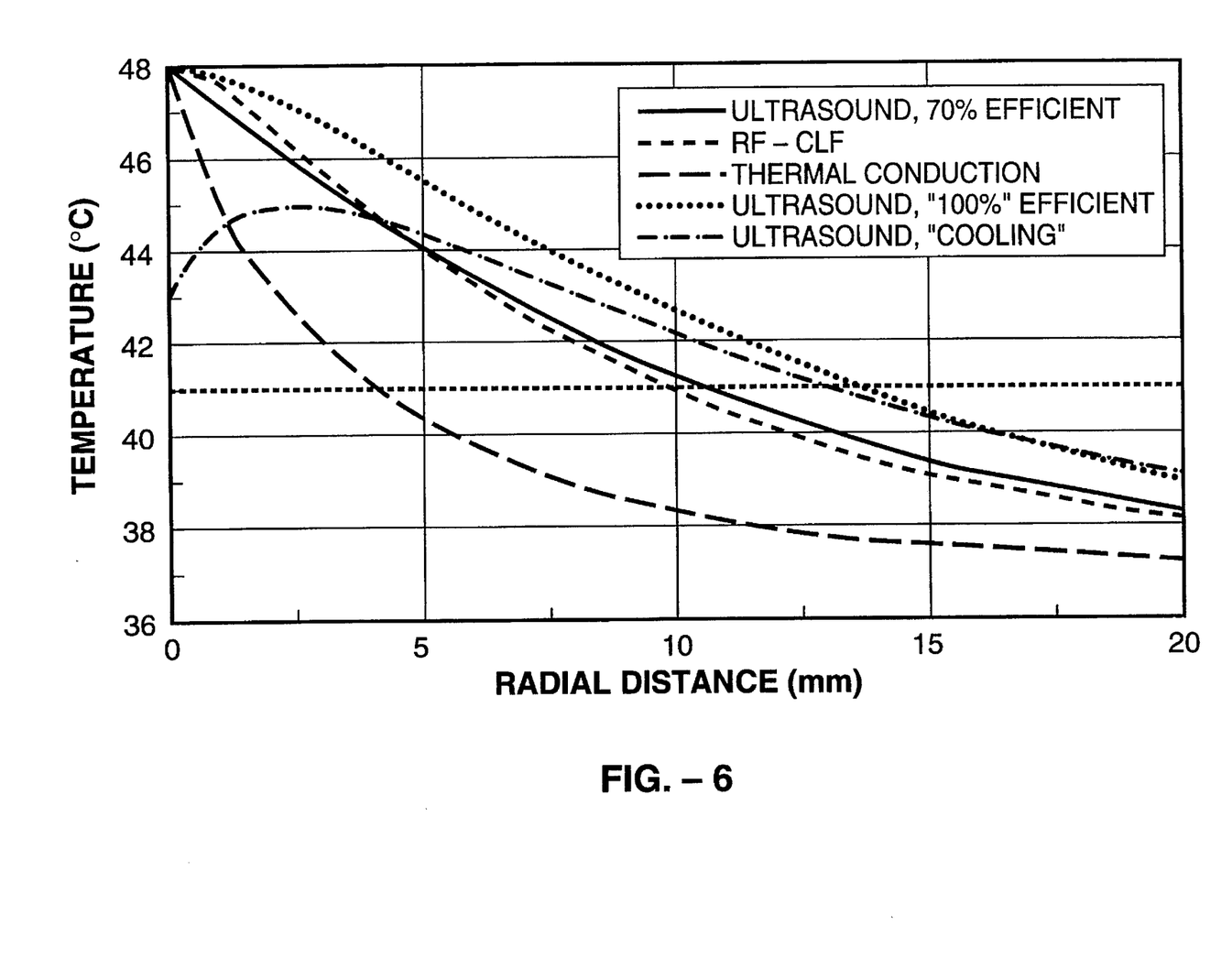
FIG. 6 shows simulated radial temperature profiles for three types of direct-coupled ultrasound applicators in accordance with the present invention compared to RF-LCF and thermal conduction sources for a source diameter of 2.6 mm and blood perfusion (w)=2 kg $m^{-3}s^{-1}$.

The simulated radial heating profiles for the following three DCIUA design configurations are shown in FIG. 6 along with profiles for conventional RF-LCF and thermal conduction interstitial sources for comparison:

1. DCIUA, 70% Efficient. This represents a direct coupled applicator operating at 7 MHz with a transducer efficiency (ratio of acoustic output power to electrical input power) of 70%, which approximates the practical upper limit.
2. DCIUA, 100% Efficient. This represents the performance of a direct-coupled applicator with a cooling mechanism capable of removing the thermal energy generated within the transducer piezoceramic (i.e., emulates 100% efficient applicator).
3. DCIUA, Active Cooling. This represents the performance of a direct-coupled applicator (70% efficient) with a cooling mechanism capable of (i) removing the thermal energy generated within the transducer piezoceramic and (ii) regulating the temperature of the applicator/tissue interface at 43° C.

These simulations demonstrated that physically realizable direct-coupled ultrasound applicators (i.e., 70% efficient), designed without a :mechanism to remove transducer self-heating, exhibit a good heating penetration compared to thermal conduction and RF-LCF techniques. The depth of this effective heating penetration is highly dependent on the efficiency of the transducer, where for the extreme case of zero efficiency these applicators behave as thermal conduction sources. The integration of a cooling mechanism to remove the effects of self-heating will significantly improve the attainable heating profile and penetration depth. Furthermore, by actively controlling (i.e., 43° C.) the temperature of the applicator/tissue interface via this "cooling" mechanism, the peak temperature can be moved away from the applicator surface to further extend the heating penetration depth.

EXAMPLE 4

Acoustic Measurements

Figure 7:
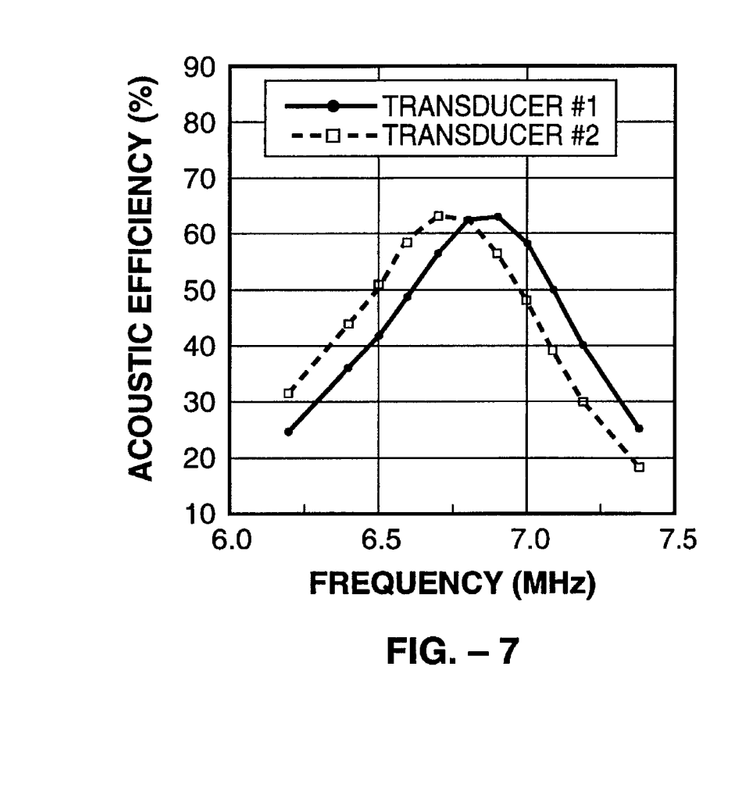
FIG. 7 shows the acoustic efficiency as a function of frequency for an applicator in accordance with the present invention.

The acoustic output power as a function of applied electrical input power and frequency was measured using the radiation force-balance technique adapted for cylindrical transducers. Measurements on a two element applicator can be seen in FIG. 7 which shows efficiencies of about 65%. At the resonant (peak efficiency) frequency, acoustic output power levels of at least 12 W per transducer were produced without applicator destruction, while power levels of only 1 to 2 W are required to produce hyperthermic temperatures. These results are encouraging, in that a non-optimized applicator has been constructed which approaches the theoretical design goal of 70% efficiency, as required for maximizing the radial heating penetration.

EXAMPLE 5

Acoustic Pressure-Squared Distributions

Figure 8:
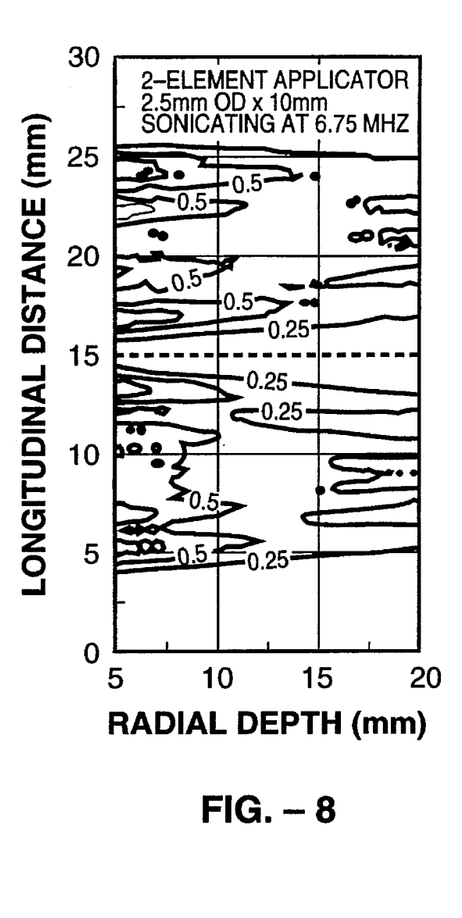
FIG. 8 shows the longitudinal acoustic beam distributions from an applicator in accordance with the present invention measured in degassed water.
Figure 9:
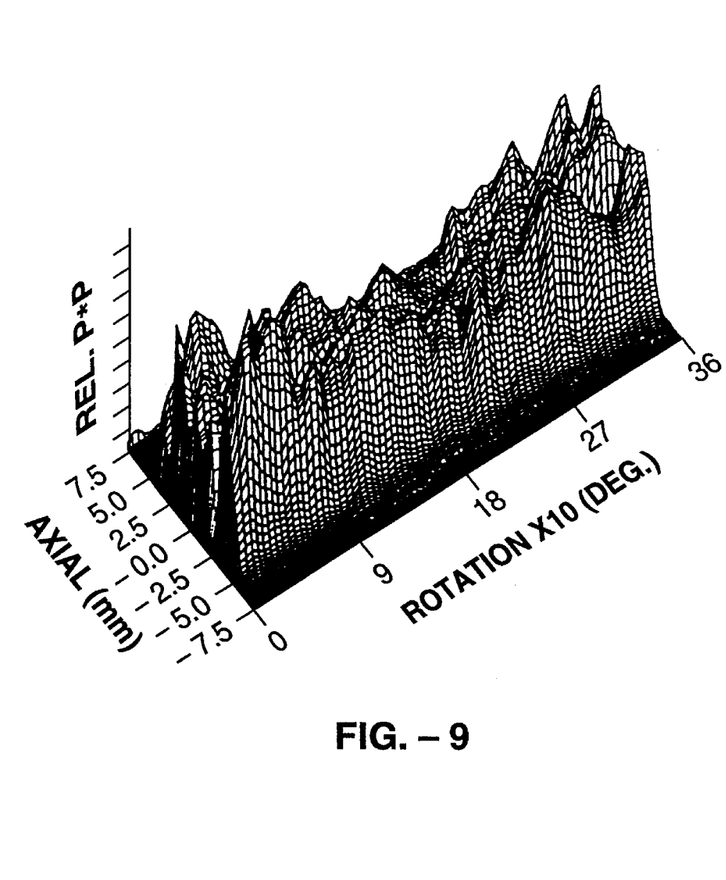
FIG. 9 shows the circumferential acoustic beam distributions from an applicator in accordance with the present invention measured in degassed water at 8 mm radial depth.

The acoustic pressure-squared distributions emitted from the apparatus were measured in degassed water by scanning a calibrated needle hydrophone under computer guidance. The measured longitudinal beam distribution for a two element prototype is shown in FIG. 8 which demonstrates the well collimated output characteristics of these transducers for precise control of the longitudinal power distribution. Since these transducers are driven with individual (incoherent) RF generators, the emitted acoustic fields are completely independent of each other. FIG. 9 shows the circumferential beam distribution around a single transducer obtained by scanning the hydrophone along the applicator length at a constant radial distance of 8 mm from the transducer surface, and incrementing the axial rotation angle from 0 to 360 degrees in 5 degree steps. These measurements indicate that the power deposition from these particular tubes is not uniform around the circumference, but varies +/−25%. This variability is mostly attributed to uneven wall thickness of the piezoceramic tubes (i.e., differing peak efficiency frequencies for different regions of the transducer), which could be minimized with future improvements in transducer manufacturing techniques and quality assurance procedures.

EXAMPLE 6

Tissue Phantom Measurements

Figure 10:
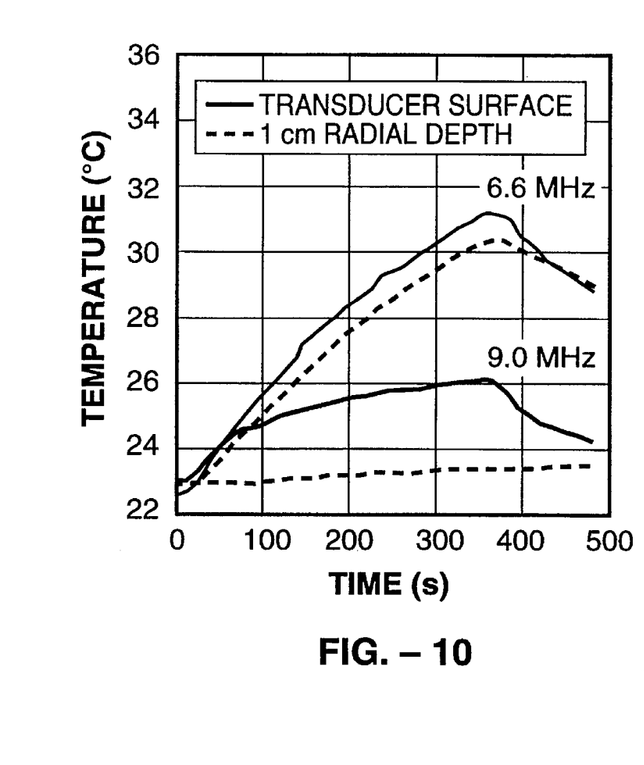
FIG. 10 shows transient temperature rises in a tissue mimicking phantom for an applicator in accordance with the present invention operated at 6.6 MHz (efficiency approximately 65%) and 9.0 MHz (efficiency approximately zero), with temperatures measured at the applicator surface and at 1.0 cm radial depth.

An "oil-in-gel" phantom which mimics the acoustic and thermal properties of liver tissue was used for transient temperature measurements. The transient temperature rises induced by an applicator implanted within the phantom are shown in FIG. 10 for operation at the frequency of peak efficiency (6.6 MHz) and off-resonant (9.0 MHz) where the transducer efficiency approaches zero were measured. The temperatures were monitored on the applicator surface and at 1 cm radial depth for each test case. These results illustrate the following: (i) at 6.6 MHz the acoustic power is a significant contributor to the temperature rise at 1 cm depth, and is not due solely to thermal conduction from transducer self heating; (ii) at 9.0 MHz there is no acoustic power deposition at 1 cm depth, and the applicator is behaving as a thermal conduction source. These studies have also demonstrated that the transducers can intentionally be operated off-resonant, where all the applied power is dissipated as transducer self-heating, to mimic conduction sources.

EXAMPLE 7

Thermal Dosimetry

In Vivo thermal dosimetry measurements were obtained in the thigh muscle of an anesthetized pig. An ultrasound catheter was implanted in the tissue, along with two 20 g stainless steel needles for thermometry sensor mapping. One needle was placed parallel to the length of the transducers at a radial distance of 10 mm from the applicator surface. The second needle was placed tangential to the surface of the distal transducer and perpendicular to the axis of the applicator. Multiple sensor constantan-manganin thermocouple probes were pulled back within these needles to map the pseudo-steady state temperature distributions after 10 minutes of heating. The surface temperature mid-length along each transducer was also monitored.

Figure 11:
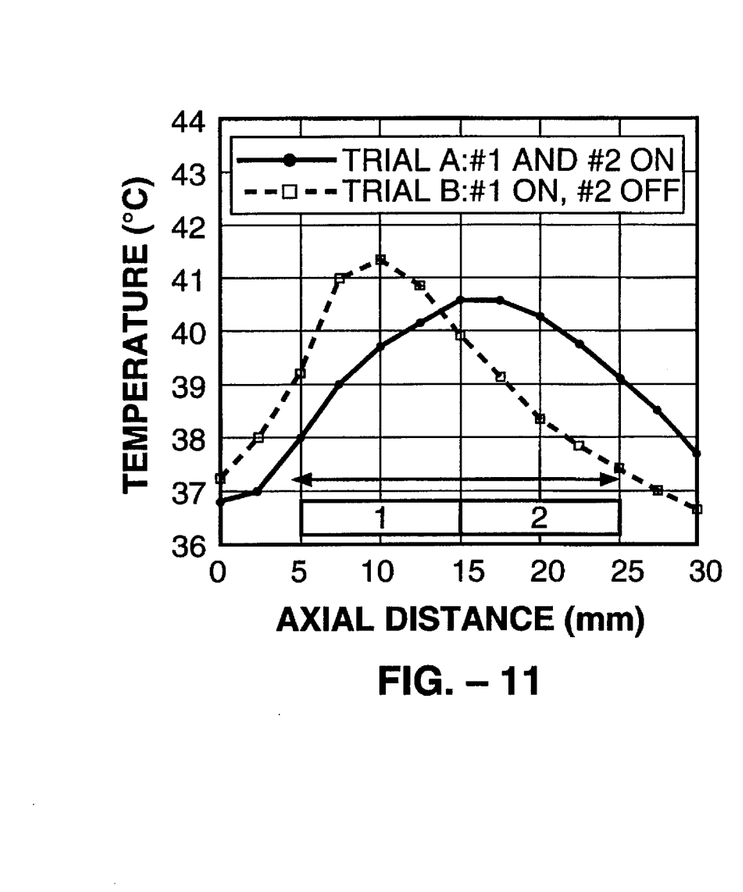
FIG. 11 shows the measured temperature profiles for a two transducer applicator in accordance with the present invention for two heating trials as a function of axial distance.
Figure 12:
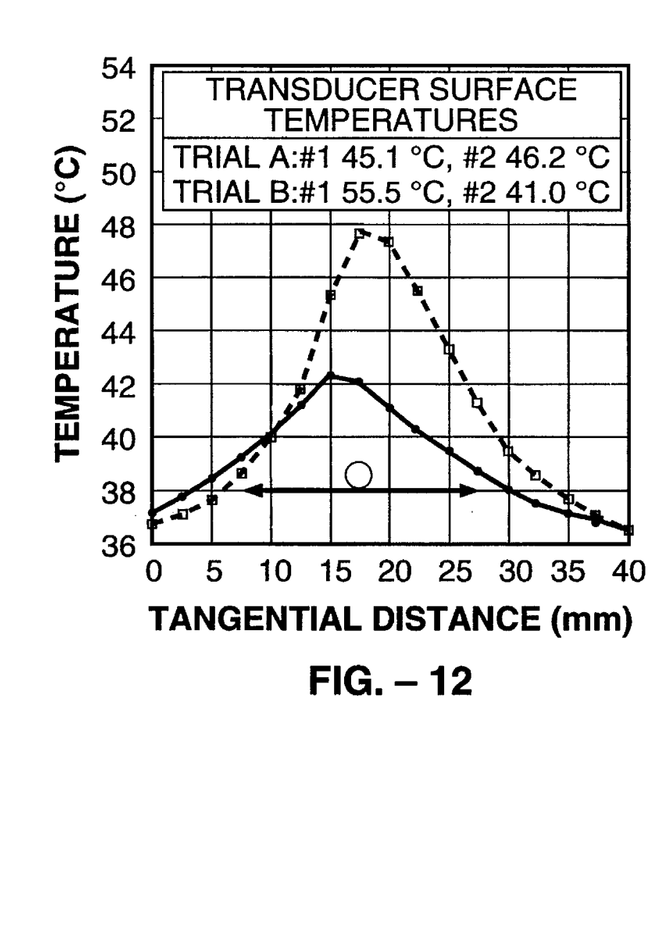
FIG. 12 shows the measured temperature profiles for a two transducer applicator in accordance with the present invention for two heating trials as a function of tangential distance.

Two heating trials were run: trial A with both transducers activated to the same power level (1 W), and trial B with only the distal transducer activated (2 W). FIG. 11 and FIG. 12 show the measured temperature profiles for trial A and trial B as a function of axial distance and tangential distance, respectively. These in vivo dosimetry studies verify that direct-coupled ultrasound applicators can provide therapeutic temperature distributions in tissue with improved radial penetration and control of the longitudinal heating pattern.

EXAMPLE 8

Radiation Compatibility

Radiation calculations and measurements have shown a transmission loss less than 2–4% for $^{192}$Ir sources within these applicators, demonstrating potential for use with iridium remote afterloaders or fixed wire sources. The loss for low activity $^{125}$I sources was >90%, indicating the impracticality of using iodine implants with these particular applicators.

EXAMPLE 9

Treatment Planning

Therapy using the applicators of the present invention can be optimized with a robust and efficient optimization based treatment planning system for thermoradiotherapy and thermal ablation procedures. Anatomical information from diagnostic images (MRI, CT, or TRUS) is used to generate 2-D geometric models of the tumor target region and surrounding normal tissue, which is then discretized to existing acoustic and biothermal models. A thermal dose prescription is then defined as a set of temperature constraints for the target and normal tissue. A minimax based optimization algorithm then determines the catheter placements and power settings for the ultrasound applicators needed to deliver the prescribed thermal dose distribution. A significant advantage of this minimax-based optimization scheme is that it minimizes the maximum temperature violation or error from the prescribed dose, not the average temperature violation which is more lenient. Additionally, the value of maximum violation provides a clinically relevant measure to quantify the merit of the treatment plan. The feasibility of this approach is demonstrated for thermal therapy of a hypothetical brain tumor. The prescribed dose was 43° to 45° C. within the entire tumor as denoted by a contrast enhanced rim in the image. The program automatically relocated an intentionally "bad" initial placement of two ultrasound applicators at the center of the tumor by moving the positions and adjusting the applied power levels until the prescribed temperature distribution was achieved.

These preliminary computational results indicate the potential of this optimization based approach to preplan the three dimensional stereotactic placement and applied power levels of multiple ultrasound applicators to improve the thermal dose distributions. This would be most critical for improving the tightness of thermal dose margins and minimizing normal tissue overheating. While these 2-D results are encouraging, important development remains to convert the 2-D thermal planning to combined 3-D thermal and radiation treatment planning.

Accordingly, the use of direct-coupled ultrasound applicators (DCIUA's) for simultaneous thermoradiotherapy is feasible, and has excellent potential to improve thermal dose distributions over those possible with previous interstitial methods which are compatible with combined therapy. Theoretical simulations and in vivo thermal dosimetry have illustrated that physically realizable applicator designs can produce effective heating distributions in perfused tissues. In order to accommodate the insertion of radiation sources within devices of acceptable size, the applicators were designed without a cooling mechanism that removes the transducer self-heating. In effect, the invention behaves as a hybrid of thermal conduction source and ultrasound source, producing radial heating profiles similar to RF applicators. The multiple element direct-coupled applicators exhibit distinct advantages resulting from (i) dynamic and spatial control of the longitudinal power deposition pattern, (ii) decreased sensitivity to applicator alignment and insertion depth in tissues, and (iii) the ability to monitor temperature at the applicator/tissue interface. Further, integration of a "cooling" scheme as described herein will increase the radial heating penetration and improve the uniformity of the thermal dose distribution. The selective heating capabilities of the ultrasound applicators combined with the long duration accumulation of thermal dose and increased radiosensitization, should improve clinical outcome. This technology can be readily adapted for use in sites such as prostate and brain, which are amenable to simultaneous thermobrachytherapy as a means of enhancing tumor response to radiation therapy.

Although the description above contains many specificities, these should not be construed as limiting the scope of the invention but as merely providing illustrations of some of the presently preferred embodiments of this invention. Thus the scope of this invention should be determined by the appended claims and their legal equivalents.

What is claimed is:

1. An apparatus for applying thermal therapy to tissue, comprising:
   (a) a tubular ultrasound transducer;
   (b) a cylindrical support member, said support member extending coaxially through said transducer;
   (c) a power lead, said power lead electrically connected to said transducer;
   (d) a sealant coating over said transducer; and
   (e) an outer cover over said sealant coating, wherein said sealant coating is disposed between and in contact with said transducer and said outer cover, and wherein said transducer is thereby directly implantable in a patient.

2. An apparatus as recited in claim 1, wherein said support member comprises tube means for receiving a source of radiation.

3. An apparatus as recited in claim 1, where said support member comprises tube means for infusing a drug into said patient.

4. An apparatus as recited in claim 1, further comprising
   (a) a second tubular ultrasound transducer, said support member extending through said second transducer, said outer cover and sealant coating covering said second transducer, said transducers being spaced apart and electrically isolated; and
   (b) a second power lead, said second power lead electrically connected to said second transducer, wherein each said transducer can be powered independently through its corresponding power lead.

5. An apparatus as recited in claim 4, further comprising:
   (a) a plurality of temperature sensors, each said temperature sensor positioned between a corresponding one of said transducers and said outer cover; and
   (b) a plurality of temperature sensor leads, each said temperature sensor lead electrically connected to a corresponding one of said temperature sensors.

6. An apparatus as recited in claim 5, further comprising means for controlling the amount of power to each said transducer independently in response to temperature measured by said temperature sensors.

7. An apparatus tier applying controlled thermal therapy to a tumor, comprising,
   (a) a support member;
   (b) a plurality of electrically isolated spaced-apart tubular ultrasound transducers received over said support member; and
   (c) a plurality of power leads, each said power lead electrically connected to a corresponding one of said transducers wherein each said transducer can be powered independently through its corresponding power lead.

8. An apparatus as recited in claim 7, where said support member comprises tube means for infusing a drug into said patient.

9. An apparatus as recited in claim 7, further comprising
   (a) a sealant coating over said transducers; and
   (b) an outer cover over said sealant coating, wherein said sealant coating is disposed between and in contact with said transducer and said outer cover, and wherein said transducer is thereby directly implantable in a patient.

10. An apparatus as recited in claim 7, wherein said support member comprises tube means for receiving a source of radiation.

11. An apparatus as recited in claim 7, further comprising:
    (a) a plurality of temperature sensors, each said temperature sensor positioned adjacent to a corresponding one of said transducers; and
    (b) a plurality of temperature sensor leads, each said temperature sensor lead electrically connected to a corresponding one of said temperature sensors.

12. An apparatus as recited in claim 11, further comprising means for controlling the amount of power to each said transducer independently in response to temperature measured by said temperature sensors.

13. A method of heating tissue in a patient for ultrasound thermal therapy using an apparatus as recited in claim 1, comprising the steps of:
    (a) inserting said apparatus directly within a target region in said tissue of said patient and directly contacting tissue with said outer cover
    (b) applying RF power to said power lead; and
    (c) heating said tissue with said apparatus.

14. A method as recited in claim 13, further comprising the step of inserting a source of radiation into said support member.

15. A method as recited in claim 13, further comprising the step of circulating a coolant through said support member.

16. A method as recited in claim 13, further comprising the step of infusing a drug into said tissue through said support member.

17. A method as recited in claim 13, further comprising the step of circulating a coolant between said support member and said transducer.

18. A method as recited in claim 13, further comprising the step of controlling heating penetration by varying the frequency of said RF power to vary acoustic efficiency which varies the ratio of acoustic to conductive heating.

19. A method for thermal therapy of tissue in a patient using an apparatus as recited in claim 6, comprising the steps of:
    (a) inserting said apparatus within a target region in said tissue of said patient;
    (b) applying RF power to said power leads; and
    (c) controlling the tissue temperature profile along the length of the apparatus by controlling the power to each said transducer independently.

20. A method as recited in claim 19, wherein said apparatus includes a sealant coating over said transducers and an outer cover over said sealant coating, and further comprising the steps of inserting said apparatus into said tissue and directly contacting tissue with said outer cover.

21. A method as recited in claim 19, further comprising the step of inserting a source of radiation into said support member.

22. A method as recited in claim 19, further comprising the step of circulating a coolant through said support member.

23. A method as recited in claim 19, further comprising the step of infusing a drug into said tissue through said support member.

24. A method as recited in claim 19, further comprising the step of circulating a coolant between said support member and said transducer.

25. A method as recited in claim 19, further comprising the step of placing said applicator in a catheter inserted into said tissue.

26. A method as recited in claim 25, further comprising the step of circulating a coolant between said applicator and said catheter.

27. A method as recited in claim 19, further comprising the step of controlling heating penetration by varying frequency of said RF power to vary acoustic efficiency which varies the ratio of acoustic to conductive heating.

28. A method of heating tissue in a patient for ultrasound thermal therapy, comprising the steps of:
  (a) inserting an ultrasound applicator within a target region in said tissue of said patient, said ultrasound applicator comprising a support member extending coaxially through an ultrasound transducer and a power lead electrically connected to said transducer;
  (b) applying RF power to said power lead;
  (c) heating said tissue with said applicator; and
  (d) infusing a drug into said tissue through said support member.

29. A method for thermal therapy of tissue in a patient, comprising the steps of:
  (a) inserting an ultrasound applicator within a target region in said tissue of said patient, said ultrasound applicator comprising a cylindrical support member extending coaxially through a plurality of spaced-apart tubular ultrasound transducers and a plurality of power leads, each said power lead electrically connected to a said one of said transducers;
  (b) applying RF power to said power leads;
  (c) heating said tissue with said applicator; and
  (d) infusing a drug into said tissue through said support member.

30. A directly implantable applicator for thermal therapy of tumors, comprising:
  (a) a plurality of electrically isolated spaced-apart tubular ultrasound transducers;
  (b) a support member extending through said transducers;
  (c) a plurality of power leads, each said power lead electrically connected to a corresponding one of said transducers wherein each said transducer can be powered independently through its corresponding power lead;
  (d) a plurality of temperature sensors, each said temperature sensor positioned adjacent to a corresponding one of said transducers;
  (e) a plurality of temperature sensor leads, each said temperature sensor lead electrically connected to a corresponding one of said temperature sensors;
  (f) a sealant coating over said transducer; and
  (g) an outer cover over said sealant coating, wherein said sealant coating is disposed between and in contact with said transducer and said outer cover, and wherein said transducer is thereby directly implantable in a patient.

31. An apparatus as recited in claim 30, further comprising means for controlling the amount of power to each said transducer independently in response to temperature measured by said temperature sensors.

32. An apparatus as recited in claim 30, wherein said support member comprises tube means for receiving a source of radiation.

33. An apparatus as recited in claim 30, where said support member comprises tube means for infusing a drug into said patient.

* * * * *